United States Patent [19]

Sale et al.

[11] 4,151,169
[45] Apr. 24, 1979

[54] PROCESS FOR PREPARING SUBSTITUTED 1,2,4-TRIAZOLE DERIVATIVES

[75] Inventors: Amedeo O. Sale; Giorgio Pifferi; Pietro Consonni; Alberto Diena, all of Milan; Bonaccorso R. Del Turco, Saronno Varese, all of Italy

[73] Assignee: Gruppo Lepetit, Milan, Italy

[21] Appl. No.: 921,911

[22] Filed: Jul. 3, 1978

Related U.S. Application Data

[60] Division of Ser. No. 720,479, Sep. 3, 1978, Pat. No. 4,119,635, which is a continuation-in-part of Ser. No. 272,105, Jul. 17, 1972, abandoned.

[51] Int. Cl.² .................................. C07D 249/08
[52] U.S. Cl. ............................................. 260/308 R
[58] Field of Search ............................... 260/308 R

[56] References Cited

U.S. PATENT DOCUMENTS 3,862,954  1/1975  Omodei-Sale ............... 260/308 R

Primary Examiner—Alton D. Rollins

[57] ABSTRACT

New 1-alkyl-3,5-disubstituted-1,2,4-triazole derivatives of following formula I

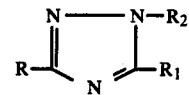

wherein R may represent phenyl; phenyl substituted by a radical selected from $(C_{1-4})$alkyl, e.g. methyl, ethyl, propyl, isopropyl, butyl, sec.-butyl, isobutyl or tert.-butyl, $(C_{1-4})$alkoxy, e.g. methoxy, ethoxy, propoxy, butoxy, isobutyloxy or tert.-butoxy, fluoro, chloro, bromo, nitro, amino, cyano, carbamoyl, carboxy, hydroxymethyl, methylenedioxy and trifluoromethyl; dichlorophenyl; dimethoxyphenyl; 3,4,5-trimethoxyphenyl;

$R_1$ may represent phenyl, phenyl substituted by a radical selected from $(C_{1-4})$alkyl as above defined, $(C_{1-4})$alkoxy as above defined, fluoro, chloro, bromo, hydroxymethyl, $(C_{2-4})$aliphatic acyloxymethyl, e.g. acetoxymethyl, propionyloxymethyl or butyryloxymethyl, carbamoyloxymethyl, bromomethyl and dimethylaminomethyl; dimethylphenyl; dimethoxyphenyl; phenyl contemporaneously substituted by o-hydroxymethyl and chloro;

$R_2$ represents a $(C_{1-4})$alkyl group as above defined; with the proviso that R and $R_1$ cannot simultaneously represent phenyl;

with the further proviso that, when R is phenyl, $R_1$ cannot be p-chlorophenyl; and processes for their preparation.

The compound of the invention have CNS depressant utility. They are especially useful as sedatives and hypnotics. Some of the compounds of the invention are also useful as anxiety relieving means.

1 Claim, No Drawings

PROCESS FOR PREPARING SUBSTITUTED 1,2,4-TRIAZOLE DERIVATIVES

CROSS REFERENCE TO RELATED APPLICATION

This is a division, of application Ser. No. 720,479 filed 9/3/78*, now U.S. Pat. 4,119,635. *which in turn is a continuation-in-part of application Ser. No. 272,105, Filed July 17, 1972, now abandoned.

SUMMARY OF THE INVENTION

This invention relates to new 1-alkyl-3,5-disubstituted-1,2,4-triazole derivatives of following formula I and to processes for their manufacture:

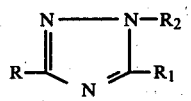   I wherein R may represent phenyl; phenyl substituted by a radical selected from ($C_{1-4}$) alkyl, e.g. methyl, ethyl, propyl, isopropyl, butyl, sec.butyl, isobutyl or tert.-butyl, ($C_{1-4}$)alkoxy, e.g. methoxy, ethoxy, propoxy, butoxy, isobutyloxy or tert.-butoxy, fluoro, chloro, bromo, nitro, amino, cyano, carbamoyl, carboxy, hydroxymethyl, methylenedioxy and trifluoromethyl; dichlorophenyl, dimethoxyphenyl; 3,4,5-trimethoxyphenyl;

$R_1$ may represent phenyl; phenyl substituted by a radical selected from ($C_{1-4}$)alkyl as above defined, ($C_{1-4}$)alkoxy as above defined, fluoro, chloro, bromo, hydroxymethyl, ($C_{2-4}$)aliphatic acyloxymethyl, e.g. acetoxymethyl, propionyloxymethyl or butyryloxymethyl, carbamoyloxymethyl, bromomethyl and dimethylaminomethyl; dimethylphenyl; dimethoxyphenyl; phenyl contemporaneously substituted by o-hydroxymethyl and chloro;

$R_2$ represents a ($C_{1-4}$)alkyl group as above defined; with the proviso that R and $R_1$ cannot simultaneously represent phenyl; with the further proviso that, when R is phenyl, $R_1$ cannot be p-chlorophenyl.

The compounds of the invention have CNS depressant utility. They are especially useful as sedative and hypnotics. Some of the compounds of the invention are also useful as anxiety relieving means.

A preferred group of compounds comprises those compounds of formula I wherein R and $R_2$ are defined as above and $R_1$ is the radical

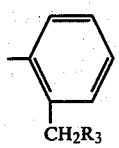

wherein $R_3$ may represent hydrogen or hydroxy.

A most preferred group of compounds comprises those compounds of formula I wherein R represents phenyl; phenyl substituted by a radical selected from methyl, methoxy, fluoro, chloro, nitro and methylenedioxy; dichlorophenyl; dimethoxyphenyl or 3,4,5-trimethoxyphenyl;

$R_1$ is the radical

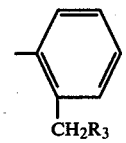

wherein $R_3$ is hydroxy, and $R_2$ stands for a methyl group. A second most preferred group of compounds comprises those compounds of formula I wherein R represents phenyl; phenyl substituted by a radical selected from methyl, methoxy, trifluoromethyl, methylenedioxy, chloro and amino; dimethoxyphenyl or 3,4,5-trimethoxyphenyl, $R_1$ is the radical

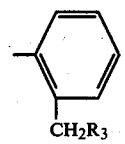

wherein $R_3$ represents hydrogen and $R_2$ stands for a methyl radical.

A general method for preparing the 1,2,4-triazoles of this invention comprises either reacting a compound of formula

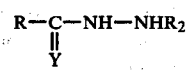   II with a compound of formula

   III or reacting a compound of formula

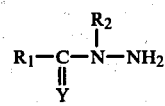   IV with a compound of formula

   V

In the above formulas II thru V the radicals R, $R_1$ and $R_2$ have the previously indicated meanings, CX is a functional group selected from carboxy, dithiocarboxy, carbonyl halide, carboxy anhydride, orthoester, imidate, thioimidate, imidoyl halide, amidino and cyano, Y is NH, and, when a compound R-CX is employed wherein the group CX contains a nitrogen atom, it represents oxygen or sulfur.

The process essentially consists in a condensation reaction, during which, depending on the nature of the reacting groups CX and Y, water, hydrogen sulfide, hydrogen halide, ammonia, alkanols, carboxylic acids or mixtures thereof are formed as by-products. The reaction is illustrated by the following scheme:

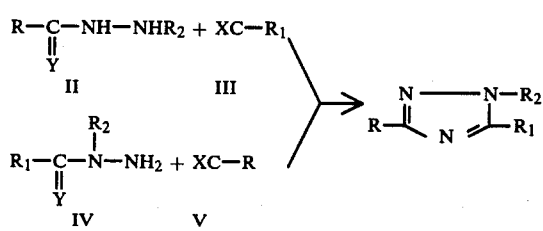

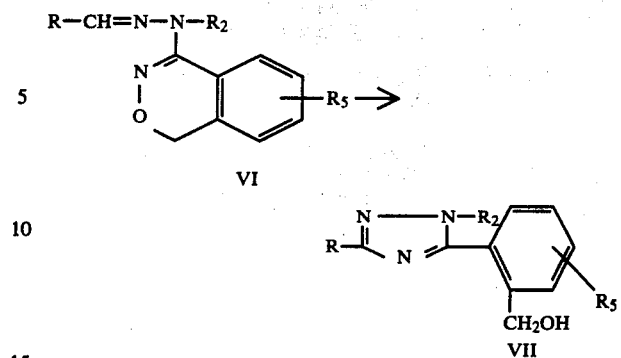

wherein R and $R_2$ are as above defined and $R_5$ is hydrogen or chloro.

A tipical method for carrying out the condensation reaction involves heating the pair of reagents of formulas II and III or IV and V in the absence of solvent at a temperature of from about 80° to about 150° C. for several hours. An excess of the compound $R_1CX$ or R—CX may be advantageously employed to speed up the reaction. In those instances where the two components can not be melted without decomposition, a high boiling inert organic solvent may be used, such, for instance, xylene, halogenated aromatic hydrocarbons, N,N-dimethylformamide and the like. Catalytic amounts of acids such as p-toluenesulfonic acid or hydrogen halides, as well as imidate or amidine acid salts may be advantageously added to speed up the cyclization rate.

The foregoing cyclization reaction may also be effected in two steps when the group CX in the compounds of formulas III and V corresponds to an acyl halide. Thus, for instance, a molecular amount of 3-chlorobenzimidic acid 2-methylhydrazide, i.e., the compound of formula (II) wherein R is 3- chlorophenyl, $R_2$ is methyl and Y is NH, is stirred for 15-25 hours at room temperature in an halogenated lower hydrocarbon solution and in the presence of an excess over the equimolecular proportion of a tertiary organic base, with a molecular amount of 2,6-dimethoxybenzoyl chloride, i.e., the compound of formula (III) wherein $R_1$ is 2,6-dimethoxyphenyl and CX corresponds to carbonyl chloride. After washing with aqueous $NaHCO_3$ and evaporating the solvent, the intermediate 2-methyl-2-(2,6-dimethoxybenzoyl)hydrazine of 3-chlorobenzimidic acid is obtained. This latter compound is cyclized by heating in an inert organic solvent at a temperature from about 80° to about 150° C. for several hours. A catalytic amount of a base such as an alkali metal hydroxide or an alkali metal alkoxide preferably sodium methoxide or ethoxide, may be used to improve the reaction rate. In some case, the obtained 1,2,4-triazole can be further transformed by generally known chemical reactions into another derivative which is encompassed by the general formula (I). As an example, the phenyl radicals R and $R_1$ may be chemically modified by introducing new substituents or by transforming a pre-existing substituent into a different functional group. If a triazole of formula I is desired wherein $R_1$ represents phenyl substituted by an o-hydroxymethyl groups, or phenyl contemporaneously substituted by o-hydroxymethyl and chloro, a further suitable method for preparing the inventive compounds involves a novel rearrangement of the hydrazones of 4-hydrazino-1H-2,3-benzoxazines of formula VI, as indicated by the following scheme:

It is quite apparent that, in this case, further chemical transformations of the obtained compounds are possible. In particular, the o-hydroxymethyl group may be transformed by known chemical procedures such as, for instance, hydrogenation, substitution, acylation and the like, into another functional group such as methyl, bromomethyl, dimethylaminomethyl, $(C_{2-4})$aliphatic acyloxy-methyl or carbamoyloxymethyl. According to the novel rearrangement process, hydrazones of benzaldehyde or substituted benzaldehydes with 4-hydrazino-1H-2,3-benzoxazines, when heated in an organic solvent which is advantageously selected from lower alkanols in the presence of an acidic catalyst, such as for instance, hydrogen chloride or p-toluene sulfonic acid, rearrange to 1,2,4-triazoles.

The final compounds are easily recovered by filtration or by evaporation of the solvent. The starting hydrazones are prepared according to the procedure described in British Pat. No. 1,227,490. The hydrazones which undergo the rearrangement may also be used in a crude state without any particular purification.

As stated before, the compounds of the invention have CNS depressant utility. More exactly, the compounds of Examples 1,2,3,5-10, 14, 31(42), 32(56), 34, 35 and 45(55) are useful as sedatives and hypnotics. These pharmacological properties were ascertained by following the operative scheme and the manipulation procedure described by S. Irwin in Psychopharmacologia (Berl.), 13, 222, 1968. Especially, there were studied the biological effects of the compounds on two of the parameters which are closely related to the above properties, namely the "spontaneous activity" and the "righting reflex". The effects of the compounds on these two parameters were expressed as $ED_{50}$ values ie., the amount of compound tested which reduces the spontaneous activity and righting reflux scores of test animals to 50% of those of the controls. The scores are the same as those reported by S. Irwin in the cited paper. For each compound it was also determined the minimal dosis which produces complete hypnosis of the test animals (MHD).

The obtained results are summarized in the following table, which also reports the toxicities of the tested substances, expressed as $LD_{50}$ values. For comparison purposes, also the activity of two known compounds was determined, The known compounds are 1-methyl-3,5-diphenyl-1,2,4-triazole (Compound A, Atkinson et al. Journ. Chem. Soc., 1954, 141, 1954) and 1-methyl-3-phenyl-5-(p-chlorophenyl)-1,2,4-triazole (Compound B, Huisgen et al., Journ. Org. Chem., 24, 892, 1959).

| Compound of Example | Decrease of spontaneous activity ED$_{50}$ mg/kg i.p.(mice) | Impairment of righting reflex ED$_{50}$ mg/kg i.p.(mice) | Minimal hypnotic dosis mg/kg i.p. (mice) | Toxicity LD$_{50}$ mg/kg i.p.(mice) |
|---|---|---|---|---|
| 1 | 60 | 100 | 300 | 1000 |
| 2 | 60 | 60 | 300 | 500 |
| 3 | 30 | 10 | 200 | 500 |
| 5 | 30 | 50 | 150 | 400 |
| 6 | 50 | 25 | 600 | 1000 |
| 7 | 30 | 20 | 80 | 500 |
| 8 | 80 | 100 | 600 | >1000 |
| 9 | 60 | 60 | 300 | 1000 |
| 10 | 60 | 40 | 300 | 1000 |
| 14 | 80 | 80 | 300 | >1000 |
| 31(42) | 60 | 50 | 300 | >1000 |
| 32(56) | 30 | 20 | 200 | >1000 |
| 34 | 30 | 20 | 60 | 200 |
| 35 | 60 | 50 | 300 | 1000 |
| 45(55) | 30 | 50 | 300 | 700 |
| A | >100 | 300 | >1000 | 1000 |
| B | >300 | >300 | >600 | >1000 |

The compounds of Examples 34 and 45(55) are also useful as anxiety relieving means. This property was investigated on the basis of the secondary response avoidance test, which was performed as described by G. Maffii, Journ. Pharm. Pharmacol., 11, 192, 1959. It has been found that the compounds of Examples 34 and 45(55) display a remarkable antianxiety effect in rats at a dose of 20 mg/kg i.p.

While the preferred routes of administration of these compounds are by mouth or parenterally, other routes may be useful employed. For oral administration the substances are embodied in pharmaceutical dosage forms such as tablets, capsules, elixirs, solution and the like. The dosage unit may contain the usual excipients such as, for example, starch, gums, alcohols, sugars, fatty acids, etc. For parenteral administration, the compounds are administered in the form of aqueous solution, admixed with conventional antioxidant, preservative, chelating and buffering agents such as, for examples, sodium formaldehyde sulfoxylate, benzyl alcohol, ethylenediaminetetraacetic acid derivatives, sodium acetate, etc. The daily dosage range is from about 1 to about 50 mg/kg of body weight, preferably administered in divided doses.

DESCRIPTION OF THE PREFERRED EMBODIMENTS

The following non-limitative examples describe in detail representative compounds of this invention and methods for their preparation.

EXAMPLE 1:

5-(2-Hydroxymethylphenyl)-1-methyl-3-phenyl-1,2,4-triazole

A suspension of 1.2 g. of 4-(2-benzylidene-1-methyl-hydrazino)-1H-2,3-benzoxazine in 12 ml. of ethanol and 12 ml. of aqueous 5% HCl is heated on a water bath for three hours. The ethanol is removed by distillation and the residue, neutralized with aqueous NaHCO$_3$, is cooled to about 0° C. The precipitate is filtered and crystallized from ethanol. M.p. 122° C. Yield 96%.

EXAMPLES 2–17:

Pursuant to the method described in Example 1, the following compounds are prepared:

| No. of Example | R | R$_1$ | R$_2$ | M.p. °C. B.p. °C. | Starting Compound |
|---|---|---|---|---|---|
| 2 | 2-Cl-phenyl | 2-(CH$_2$OH)-phenyl | CH$_3$ | 84–85 | 4-[2-(2-chlorobenzylidene)-1-methylhydrazino]-1H-2,3-benzoxazine |
| 3 | 3-Cl-phenyl | 2-(CH$_2$OH)-phenyl | CH$_3$ | 91–92 | 4-[2-(3-chlorobenzylidene)-1-methylhydrazino]-1H-2,3-benzoxazine |
| 4 | 4-Cl-phenyl | 2-(CH$_2$OH)-phenyl | CH$_3$ | 127–128 | 4-[2-(4-chlorobenzylidene)-1-methylhydrazino]-1H-2,3-benzoxazine |

-continued

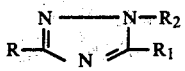

| No. of Example | R | R₁ | R₂ | M.p. °C. B.p. °C. | Starting Compound |
|---|---|---|---|---|---|
| 5 | 3-fluorophenyl | 2-(hydroxymethyl)phenyl | CH₃ | 95–97 | 4-[2-(3-fluorobenzylidene)-1-methylhydrazino]-1H-2,3-benzoxazine |
| 6 | 2-methylphenyl | 2-(hydroxymethyl)phenyl | CH₃ | 125–126 | 4-[2-(2-methylbenzylidene)-1-methylhydrazino]-1H-2,3-benzoxazine |
| 7 | 3-methylphenyl | 2-(hydroxymethyl)phenyl | CH₃ | 105–106 | 4-[2-(3-methylbenzylidene)-1-methylhydrazino]-1H-2,3-benzoxazine |
| 8 | 4-methylphenyl | 2-(hydroxymethyl)phenyl | CH₃ | 157–158 | 4-[2-(2-methylbenzylidene)-1-methylhydrazino]-1H-2,3-benzoxazine |
| 9 | 3-methoxyphenyl | 2-(hydroxymethyl)phenyl | CH₃ | 110–112 | 4-[2-(3-methoxybenzylidene)-1-methylhydrazino]-1H-2,3-benzoxazine |
| 10 | 3-nitrophenyl | 2-(hydroxymethyl)phenyl | CH₃ | 162–163 | 4-[2-(3-nitrobenzylidene)-1-methylhydrazino]-1H-2,3-benzoxazine |
| 11 | 4-nitrophenyl | 2-(hydroxymethyl)phenyl | CH₃ | 175–176 | 4-[2-(4-nitrobenzylidene)-1-methylhydrazino]-1H-2,3-benzoxazine |
| 12 | 3,4-dichlorophenyl | 2-(hydroxymethyl)phenyl | CH₃ | 118–119 | 4-[2-(3,4-dichlorobenzylidene)-1-methylhydrazino]-1H-2,3-benzoxazine |
| 13 | 3,5-dimethoxyphenyl | 2-(hydroxymethyl)phenyl | CH₃ | 150–151 | 4-[2-(3,5-dimethoxybenzylidene)-1-methylhydrazino]-1H-2,3-benzoxazine |
| 14 | 3,4-methylenedioxyphenyl | 2-(hydroxymethyl)phenyl | CH₃ | 122–123 | 4-[2-(3,4-methylenedioxybenzylidene)-1-methylhydrazino]-1H-2,3-benzoxazine |

-continued $$\underset{R}{\overset{N-----N-R_2}{\underset{N}{\|}}}R_1$$

| No. of Example | R | R₁ | R₂ | M.p. °C. B.p. °C. | Starting Compound |
|---|---|---|---|---|---|
| 15 | 3,4,5-tri(CH₃O)-phenyl | 2-(CH₂OH)-phenyl | CH₃ | 174–176 | 4-[2-(3,4,5-trimethoxybenzylidene)-1-methylhydrazino]-1H-2,3-benzoxazine |
| 16 | phenyl | 4-Cl, 2-(CH₂OH)-phenyl | CH₃ | 131–132 | 4-(2-benzylidene)-1-methylhydrazino]-6-chloro-1H-2,3-benzoxazine |
| 17 | 4-O₂N-phenyl | 4-Cl, 2-(CH₂OH)-phenyl | CH₃ | 209–210 | 4-[2-(4-nitrobenzylidene)-1-methylhydrazino]-6-chloro-1H-2,3-benzoxazine |

EXAMPLE 18:

5-(2-Acetoxymethylphenyl)-1-methyl-3-(4-nitrophenyl)-1,2,4-triazole 0.5 Grams of 5-(2-hydroxymethylphenyl)-1-methyl-3-(4-nitrophenyl)-1,2,4-triazole are heated on a steam bath for 3 hours with 5 ml. of acetic anhydride and the residue obtained after evaporation to dryness is crystallized from 20 ml. of ethanol. Yield 88%. M.p. 126°–127° C.

EXAMPLE 19:

5-(2-Carbamyloxymethylphenyl)-1-methyl-3-(o-tolyl)-1,2,4-triazole

Dry halogen chloride is bubbled for 30 minutes at about 0°–5° C. into a suspension of 2.8 g. of 1-methyl-3-(o-tolyl)-5-(2-hydroxymethylphenyl)-1,2,4-triazole and 1.82 g. of sodium cyanate in 50 ml. of chloroform. After standing for 15 minutes at room temperature, the solution is evaporated and the residue dissolved in diethyl ether. After washing the ether solution with aqueous sodium bicarbonate and drying over Na₂SO₄, the solvent is evaporated and the crude product is crystallized from benzene. M.p. 126°–128° C. Yield 68%.

EXAMPLES 20–24:

According to the procedure described in Example 19, the following compounds are prepared:

$$\underset{R}{\overset{N-----N-R_2}{\underset{N}{\|}}}R_1$$

| No. of Example | R | R₁ | R₂ | M.p. °C. B.p. °C. | Starting Material 5-(2-hydroxymethylphenyl)-1,2,4-triazole |
|---|---|---|---|---|---|
| 20 | 3-CH₃-phenyl | 2-(CH₂OCONH₂)-phenyl | CH₃ | 188–189 | 1-methyl-3-(m-tolyl)- |
| 21 | 4-CH₃-phenyl | 2-(CH₂OCONH₂)-phenyl | CH₃ | 182–183 | 1-methyl-3-(p-tolyl)- |
| 22 | 2-Cl-phenyl | 2-(CH₂OCONH₂)-phenyl | CH₃ | 149–150 | 1-methyl-3-(2-chlorophenyl)- |

-continued

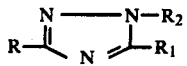

| No. of Example | R | R₁ | R₂ | M.p. °C. B.p. °C. | Starting Material 5-(2-hydroxymethylphenyl)-1,2,4-triazole |
|---|---|---|---|---|---|
| 23 | 3-Cl-C₆H₄- | 2-(CH₂OCONH₂)-C₆H₄- | CH₃ | 192–193 | 1-methyl-3-(3-chlorophenyl)- |
| 24 | 4-Cl-C₆H₄- | 2-(CH₂OCONH₂)-C₆H₄- | CH₃ | 173–174 | 1-methyl-3-(4-chlorophenyl)- |

EXAMPLE 25:

1-Methyl-3-phenyl-5-(2-bromomethylphenyl)-1,2,4-triazole

To 300 ml. of dichloromethane saturated with dry hydrogen bromide 7 g. of 1-methyl-3-phenyl-5-(2-hydroxymethylphenyl)-1,2,4-triazole are added. The solution is allowed to stand at room temperature for a night and after washing with aqueous sodium bicarbonate and then with water it is dried over sodium sulfate. Evaporation of the solvent and crystallization from hexane afford the title compound. M.p. 83°–85° C. Yield 84%.

EXAMPLES 26–28:

By operating as in Example 25, the following compounds are prepared starting from their corresponding 2-hydroxymethyl derivatives:

(26) 5-(2-bromomethylphenyl)-1-methyl-3-(m-tolyl)-1,2,4-triazole. M.p. 116°–117° C. Yield 85%.

(27) 5-(2-bromomethylphenyl)-1-methyl-3-(3-chlorophenyl)-1,2,4-triazole. M.p. 126°–128° C. Yield 71%.

(28) 5-(2-bromomethylphenyl)-1-methyl-3-(4-nitrophenyl)-1,2,4-triazole. M.p. 285° C. Yield 42%.

EXAMPLE 29:

1-Methyl-3,5-bis(o-tolyl)-1,2,4-triazole 2.81 Grams of 1-methyl-3-(o-tolyl)-5-(2-hydroxymethylphenyl)-1,2,4-triazole and 0.365 g. of dry hydrogen chloride in 100 ml. of ethanol are hydrogenated in the presence of 1 g. of 10% palladiated charcoal as a catalyst.

After taking up of one molecular amount of hydrogen, the catalyst is filtered off and the filtrate evaporated to dryness. The residue is taken up with a NaHCO₃ solution and extracted with diethyl ether; after drying and evaporation of the solvent, the title compound is distilled at 170° C./0.08 mm Hg. Yield 76%.

EXAMPLES 30–38:

Pursuant to the procedure described in Example 29 and starting from their corresponding 2-hydroxymethylphenyl compounds, the following derivatives are prepared:

(30) 1-Methyl-3-(o-tolyl)-5-phenyl-1,2,4-triazole. B.p. 170° C./0.1 mm Hg. Yield 80%.

(31) 1-Methyl-5-(o-tolyl)-3-phenyl-1,2,4-triazole, B.p. 160° C./0.1 mm Hg. Yield 76%.

(32) 1-Methyl-3-(m-tolyl)-5-(o-tolyl)-1,2,4-triazole. M.p. 80°–81° C. Yield 86%.

(33) 1-Methyl-3-(p-tolyl)-5-(o-tolyl)-1,2,4-triazole. M.p. 139°–140° C. Yield 78%.

(34) 1-Methyl-3-(3-aminophenyl)-5-(o-tolyl)-1,2,4-triazole. M.p. 128°–130° C. Yield 51%. In this case the compound is prepared by using as a starting material 1-methyl-3-(3-nitrophenyl)-5-(2-hydroxymethylphenyl)-1,2,4-triazole and hydrogenating in a single step the nitro and the hydroxymethyl group.

(35) 1-Methyl-3-(3-methoxyphenyl)-5-(o-tolyl)-1,2,4-triazole B.p. 190° C./0.03 mm Hg. Yield 79%.

(36) 1-Methyl-3-(3,5-dimethoxyphenyl)-5-(o-tolyl)-1,2,4-triazole. M.p. 104°–105° C. Yield 72%.

(37) 1-Methyl-3-(3,4-methylenedioxyphenyl)-5-(o-tolyl)-1,2,4-triazole. M.p. 96°–97° C. Yield 63%.

(38) 1-Methyl-3-(3,4,5-trimethoxyphenyl)-5-(o-tolyl)-1,2,4-triazole. M.p. 175°–176° C. Yield 70%.

EXAMPLE 39:

1-Methyl-5-(2-dimethylaminomethylphenyl)-3-(3-chlorophenyl)-1,2,4-triazole.

To a solution of 4. g. of 1-methyl-3-(3-chlorophenyl)-5-(2-bromomethylphenyl)-1,2,4-triazole in 50 ml. of anhydrous benzene, 8.8 ml. of a benzene solution containing 20% of dimethylamine are added maintaining the temperature of about 5°–10° C. The mixture was maintained under stirring for 16 hours and then washed with 10% sodium hydroxide and with an aqueous solution of sodium chloride. The organic solution is dried over sodium sulfate and then evaporated. The crude product is purified by distillation at 175° C./0.07 mm Hg. Yield 86%.

EXAMPLE 40–41:

The following compounds are prepared according to the method described in Example 39 by employing their corresponding 2-bromomethylphenyl derivatives as the starting materials:

(40) 1-methyl-5-(2-dimethylaminomethylphenyl)-3-phenyl-1,2,4-triazole. B.p. 180° C./0.07 mm Hg. Yield 96%.

(41) 1-methyl-5-(2-dimethylaminomethylphenyl)-3-(m-tolyl)-1,2,4-triazole. B.p. 180° C./0.01 mm Hg. Yield 95%.

EXAMPLE 42:

1-Methyl-5-(o-tolyl)-3-phenyl-1,2,4-triazole

A mixture of 0.56 g. of benzimidic acid 2-methylhydrazide hydrochloride and 3.8 g. of o-toluic acid chloride is heated under stirring at about 120° C. After cooling and addition of diethyl ether, the hydrochloride of the triazole is collected on filter and then suspended in a sodium bicarbonate aqueous solution. The free base is extracted with diethyl ether and the organic phase, after drying over sodium sulfate, is evaporated. The crude compound is purified by distillation at 160° C./0.1 mm Hg. Yield 76%.

EXAMPLES 43–53:

The following triazoles are prepared in accordance with the method described in Example 42 by using the corresponding acid chlorides and benzimidic acid hydrazides:

EXAMPLE 55:

1-Methyl-3-(3-chlorophenyl)-5-(o-tolyl)-1,2,4-triazole

A mixture of 6.85 g. of 1-methyl-1-(o-toluyl)-hydrazine, 13.8 g. of m-chlorobenzimidic acid ethyl ester and 1.8 g. of the hydrochloride of m-chlorobenzimidic acid ethyl ester is heated with stirring under vacuum for 18 hours and simultaneously ethanol and m-chlorobenzonitrile are distilled off. Then, maintaining the temperature at about 65° C., 40 ml. of ethanol are added followed by a sodium ethylate solution prepared from 0.336 g. of sodium and 20 ml. of ethanol. The mixture is refluxed for 6 hours and after standing over night, the insoluble precipitate is filtered off. The filtrate is evaporated to dryness. The residue is dissolved in 100 ml. of diethyl ether and after washing the organic layer successively with aqueous 5% $Na_2CO_3$, 5% HCl and water, the solution is dried over sodium sulfate. The crude product obtained by evaporation of the diethyl ether solution is

| Example No. | 1,2,4-Triazole | B.p.: °C./mm Hg M.p.: °C. | Acid chloride | 2-Methylhydrazide of |
|---|---|---|---|---|
| 43 | 1-methyl-3-(o-tolyl)-5-phenyl- | 170/0.1 | benzoic | o-tolumidic acid |
| 44 | 1-methyl-3-(3-trifluoromethyl)-5-(o-tolyl)- | 87–88 | o-toluic | 3-trifluoromethylbenzimidic acid |
| 45 | 1-methyl-3-(3-chlorophenyl)-5-(o-tolyl) | 75–76 | o-toluic | 3-chlorobenzimidic acid |
| 46 | 1-methyl-5-(2,4-dimethylphenyl)-3-(m-tolyl) | 105–106 | 2,4-dimethylbenzoic | m-toluimidic acid |
| 47 | 1-methyl-3,5-bis(m-tolyl) | 72–73 | m-toluic | m-toluimidic acid |
| 48 | 1-methyl-3-(3-chlorophenyl)-5-(2,4-dimethylphenyl)- | 47–48 | 2,2-dimethylbenzoic | 3-chlorobenzimidic acid |
| 49 | 1-methyl-3,5-bis(3-chlorophenyl)- | 88–89 | 3-chlorobenzoic | 3-chlorobenzimidie acid |
| 50 | 1-methyl-3-(o-tolyl)-5-m-tolyl)- | 170/0.02 | m-toluic | o-toluimidie acid |
| 51 | 1-methyl-3-(o-tolyl)-5-p-tolyl)- | | p-toluic | o-toluimidic acid |
| 52 | 1-methyl-3-(o-tolyl)-5-(p-chlorophenyl)- | 76–78 | p-chlorobenzoic | o-toluimidic acid |
| 53 | 1-methyl-3-(o-tolyl)-5-(o-chlorophenyl)- | | o-chlorobenzoic | o-toluimidic |

The benzimidic acid hydrazides employed as the starting materials for preceding Examples 42–53 are prepared according to the method described by N. R. Atkinson in J. Chem. Soc. 3319 (1954). The following were so prepared:
o-toluimidie acid 2-methylhydrazine hydrochloride M.p. 85°–88° C. with decomposition
m-trifluoromethylbenzimidic acid 2-methylhydrazide M.p. 57°–61° C.
m-chlorobenzimidic acid 2-methylhydrazide M.p. 110°–112° C.
m-toluimidic acid 2-methylhydrazide M.p. 79°–81° C.

EXAMPLE 54:

1-Methyl-3-(o-tolyl)-5-phenyl-1,2,4-triazole

A mixture of 1.14 g. of o-toluimidic acid ethyl ester, 1.14 g. of 1-methyl-1-benzoylhydrazine and 0.1 g. of o-toluimidic acid ester hydrochloride, as a catalyst, is heated at about 100° C. for three hours under reduced pressure (about 200 mm Hg) and then at about 120° C. for five hours. The raw material is taken up with diethyl ether and the organic solution is washed with aqueous sodium bicarbonate and then dried over $Na_2SO_4$. After evaporation of the solvent, the product is distilled at 170° C./0.1 mm Hg. Yield 32%.

crystallized from ethanol. Yield 66%. M.p. 77°–78° C.

EXAMPLES 56–57:

By following the procedure of Example 55, the following triazoles are prepared:
(56) 1-methyl-3-(m-tolyl)-5-(o-tolyl)-1,2,4-triazole. M.p. 80°–81° C., by reacting 1-methyl-1-(o-toluyl)-hydrazine with m-toluimidic acid ethyl ester and its corresponding hydrochloride as a catalyst.
(57) 1-methyl-5-(3-chlorophenyl)-3-(o-tolyl)-1,2,4-triazole
M.p. 86°–88° C., by reacting 1-methyl-1-(3-chlorobenzoyl)-hydrazine with toluimidic acid ethyl ester and its corresponding hydrochloride as a catalyst.

EXAMPLE 58:

1-Methyl-3-(3-chlorophenyl)-5-(2,6-dimethoxyphenyl)-1,2,4-triazole

To a solution of 5.08 g. of 3-chlorobenzimidic acid 2-methyl-hydrazide and 4.3 ml. of triethylamine in 85 ml. of dichloromethane, 5.6 g. of 2,6-dimethoxybenzoyl chloride in 50 ml. of dichloromethane are added under stirring. The agitation is continued for about 20 hours. The solution is then washed with diluted sodium bicarbonate and with water and dried over $Na_2SO_4$. The solvent is evaporated and the product crystallized from 1,2-dimethoxyethane. M.p. 172°–173° C. Three grams of the so obtained 1-methyl-1-(2,6-dimethoxybenzoyl)-2-(3-chlorobenzimidoyl)-hydrazine is added to a solution of 0.06 g. of sodium in 37 ml. of n-pentanol and the mixture is heated at 150° C. for 6 hours. The solvent is then distilled off and the crude product, after treatment with water, is collected on a filter. Crystallization from diisopropyl ether affords a product which melts at 147°-148° C. Overall yield 47%. This compound has been prepared also through a one-step process according to the method described in Example 54 by reacting 3-chlorobenzimidic acid ethyl ester with 1-methyl-1-(2,6-dimethoxybenzoyl)hydrazine. The starting imidates of Examples 55 to 57 and the corresponding salts are prepared according to literature methods. (Pinner, "Die Imidoaether und Ihre Derivate" - R. Oppenheim, Berlin, 1892; L. Weintraub et al., J. Org. Chem., Vol. 33, No. 4, page 1679, 1968). The starting 1-methyl-1-benzoylhydrazines are prepared according to the method described by A. R. MacCarthy et al. In J.C.S.(B) 1185 (1969) for 1-methyl-1-benzoylhydrazine. The following new compounds have been so prepared:

1-methyl-1-(o-toluyl)hydrazine hydrochloride. M.p. 190°-191° C.

1-methyl-1-(3-chlorobenzoyl)hydrazine. B.p. 130°-140° C./0.05 mm Hg.

We claim:

1. A process for preparing compounds of formula

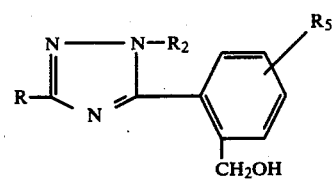

wherein R may represent:

phenyl; phenyl substituted by a radical selected from $(C_{1-4})$alkyl, $(C_{1-4})$alkoxy, fluoro, chloro, bromo, nitro, amino, cyano, carbamoyl, carboxy, hydroxymethyl, methylenedioxy and trifluoromethyl; dichlorophenyl; dimethoxyphenyl;

3,4,5-trimethoxyphenyl;

$R_2$ represents a $(C_{1-4})$alkyl group and $R_5$ stands for hydrogen or chloro, which comprises subjecting to thermal or acid-catalyzed rearrangement a benzoxazine derivative of formula

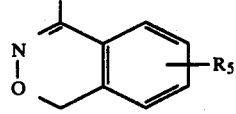

wherein R, $R_2$ and $R_5$ are as above defined.

* * * * *

UNITED STATES PATENT AND TRADEMARK OFFICE
CERTIFICATE OF CORRECTION

PATENT NO. : 4,151,169

DATED : April 24, 1979

INVENTOR(S) : Amedeo Omodei Sale, et al.

It is certified that error appears in the above-identified patent and that said Letters Patent are hereby corrected as shown below:

First page, second column, last paragraph first line, "compound" should read --compounds--.

Column 1, line 2, should read -- 9/3/78, now U.S. Pat. 4,119,635, which in turn is a --.

Column 3, line 45, "(2,6-dimethoxybenzoyl)hydrazine" should read -- (2,6-dimethoxybenzoyl)hydrazide --.

Column 4, line 54, "reflux" should read --reflex--.

Column 8, Example No. 8, under the subheading Starting Compound, should read -- 4-[2-(4-methylbenzylidene)-1-methylhydrazino] --.

Column 9, line 43, "Dry halogen" should read --Dry hydrogen--.

Column 12, line 50, "was" should read --is--.

Column 13, line 49, should read, -- o-toluimidic acid 2-methylhydrazide hydrochloride --.

Column 14, Example No. 48, under the subheading Acid chloride, should read -- 2,4-dimethylbenzoic --.

Column 14, Example No. 43, under the subheading 2-Methylhydrazide of, should read -- o-toluimidic acid --.

Column 14, Example No. 49, under the subheading 2-Methylhydrazide of, should read -- 3-chlorobenzimidic acid --.

UNITED STATES PATENT AND TRADEMARK OFFICE
CERTIFICATE OF CORRECTION

PATENT NO. : 4,151,169

DATED : April 24, 1979

INVENTOR(S) : Amedeo Omodei Sale, et al.

It is certified that error appears in the above-identified patent and that said Letters Patent are hereby corrected as shown below:

Column 14, Example No. 50, under the subheading 2-Methylhydrazide of, should read, -- o-toluimidic acid --.

Column 14, Example No. 53, under the subheading 2-Methylhydrazide of, should read, -- o-toluimidic acid --.

Signed and Sealed this

Thirtieth Day of October 1979

[SEAL]

Attest:

RUTH C. MASON
Attesting Officer

LUTRELLE F. PARKER
Acting Commissioner of Patents and Trademarks